(12) United States Patent
Pathak et al.

(10) Patent No.: US 8,308,664 B2
(45) Date of Patent: Nov. 13, 2012

(54) TREMOR STABILIZING SYSTEM FOR HANDHELD DEVICES

(75) Inventors: Anupam Pathak, Ann Arbor, MI (US); Jonathan Luntz, Ann Arbor, MI (US); Diann Brei, Milford, MI (US); Tian Shen, Princeton, NJ (US); Sarah Napier, Clarkston, MI (US); Rajiv Ghosh, Ann Arbor, MI (US); Sei Jin Park, Ann Arbor, MI (US)

(73) Assignee: The Regents of the University of Michigan, Ann Arbor, MI (US)

( * ) Notice: Subject to any disclaimer, the term of this patent is extended or adjusted under 35 U.S.C. 154(b) by 264 days.

(21) Appl. No.: 12/716,860

(22) Filed: Mar. 3, 2010

(65) Prior Publication Data

US 2010/0228362 A1    Sep. 9, 2010

Related U.S. Application Data

(60) Provisional application No. 61/157,064, filed on Mar. 3, 2009.

(51) Int. Cl.
*A61B 5/103* (2006.01)
*A61B 5/117* (2006.01)

(52) U.S. Cl. ........................................................ 600/595
(58) Field of Classification Search .................. 600/587, 600/595
See application file for complete search history.

(56) References Cited

U.S. PATENT DOCUMENTS

| | | | | |
|---|---|---|---|---|
| 6,234,045 | B1 * | 5/2001 | Kaiser | 74/572.2 |
| 6,458,089 | B1 * | 10/2002 | Ziv-Av | 600/595 |
| 7,563,097 | B2 * | 7/2009 | Lavigna et al. | 434/16 |

\* cited by examiner

*Primary Examiner* — Jeffrey G Hoekstra
*Assistant Examiner* — Charles Becker
(74) *Attorney, Agent, or Firm* — Reising Ethington P.C.

(57) ABSTRACT

A handheld device for canceling unintentional muscle movement. The device includes a base comprising a handgrip for a user to hold, a gripping element linked to the base for releasably connecting the handheld device to an object, a sensor that detects movement of the base, a controller linked to the sensor, and at least one actuator that operates under control of the controller to cause movement of the gripping element in a direction that at least partially counteracts the detected movement of the base.

21 Claims, 7 Drawing Sheets

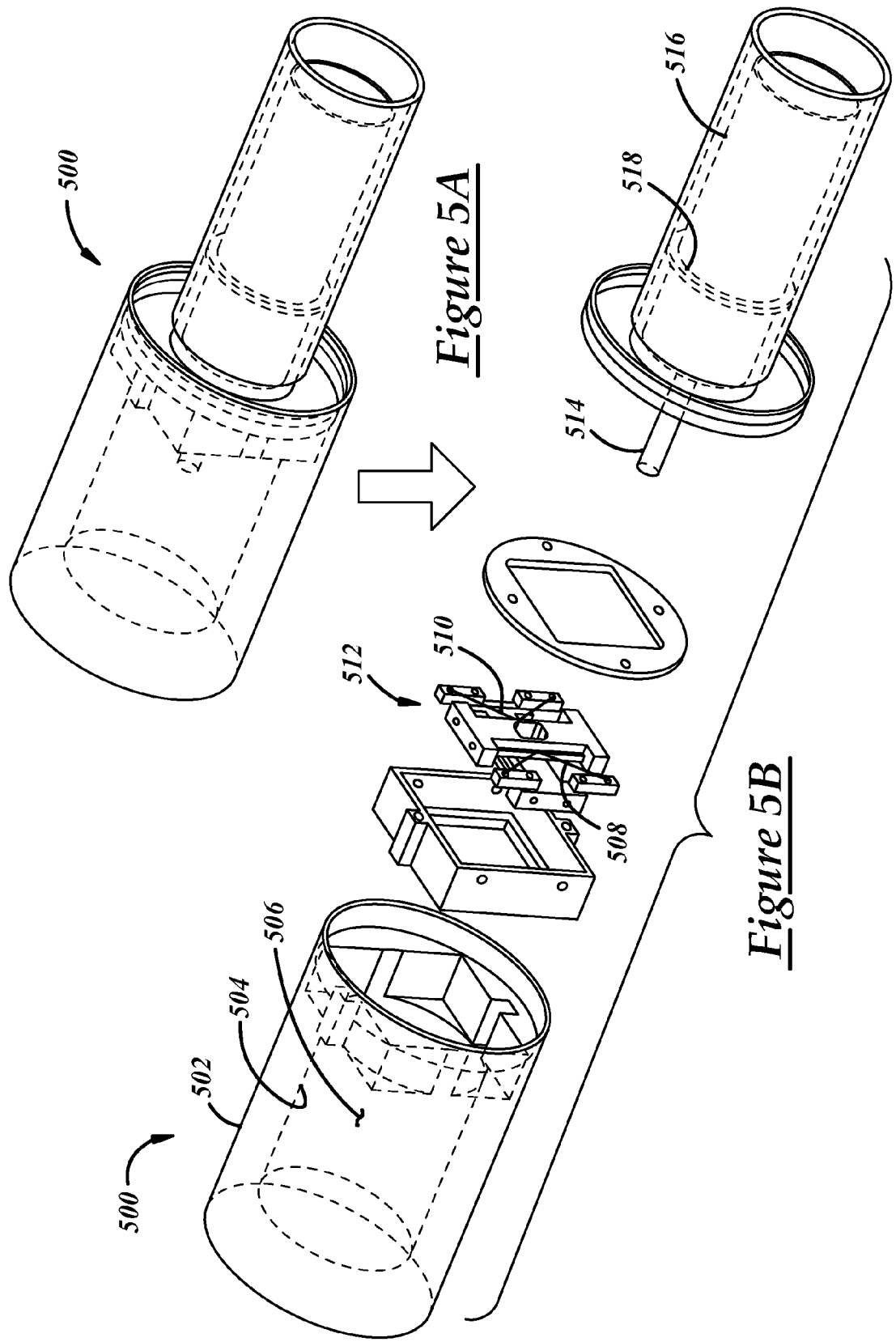

TREMOR STABILIZING SYSTEM FOR HANDHELD DEVICES

CROSS-REFERENCE TO RELATED APPLICATION

This application claims the benefit of U.S. Provisional Patent Application No. 61/157,064, filed Mar. 3, 2009, the complete contents of which are hereby incorporated by reference.

TECHNICAL FIELD

This invention relates generally to handheld devices that can help compensate for uncontrollable tremors that afflict patients.

BACKGROUND OF THE INVENTION

Tremors of the type considered herein are unintentional muscle movements in the human body. Both healthy individuals and people diagnosed with neurologically caused disorders suffer from tremors. Essential tremor is a common tremor type and as many as ten million people in the U.S. alone suffer from this type of tremor. It is especially common among people 65 years old and older and can be found in as many as 50% of this age group. The effects of essential tremor can cause significant disability. People diagnosed with this tremor can have trouble performing necessary functions, such as eating and drinking Tremor also interferes with daily activities such as using keys, typing on a computer, or applying make-up, causing a reduction in the quality of life for those people. Additionally, individuals affected by tremor who work in occupations requiring fine muscle control (e.g. artists, surgeons, musicians, drafters) are often forced to retire as a result.

Various treatments for essential tremor exist, but they have shown limited effectiveness. For example, pharmacologic treatments are known to help alleviate unwanted muscle motion. However, the effectiveness of these treatments can vary and they are typically prescribed on a trial-and-error basis. Additionally, side effects can be significant because the beta blockers commonly used for essential tremor mask signs of hypoglycemia and may cause memory loss and confusion in the elderly. For patients who are resistant to drug treatment or have severely disabling tremor, pharmacologic solutions alone are often inadequate. In these cases surgical treatments such as thalamotomy and thalamic deep brain stimulation may be used. But these treatments involve operative and post-operative risks and are not always desirable.

Despite current treatment options, many patients possess tremor that is not curable or they may decline treatment because they consider the risks and side-effects to be too great. One approach for this group is the use of tremor suppression devices that physically force a person's tremor to cease. These devices are supported by a large unmoving (grounded) mass and deliver an appropriately timed and measured force against the user's affected body part. For instance, physically grounded joysticks supported by a heavy table have been developed to mechanically dampen a person's tremor to aid in the overall control of electronic wheelchairs. In another example, wearable prosthetics suppress tremor using actively controlled forces that are produced from the bulk of the operator's body. While physically grounded devices are capable of forcing a person's tremor to cease, they suffer from some disadvantages. One significant disadvantage is user discomfort or pain that occurs when relatively large forces are applied to an affected limb. Another problem is that these devices typically do not distinguish between intended and unintended motions. Therefore, patients encounter resistance to all regular directed movements making the experience of wearing the device awkward and obtrusive. Additionally, most grounded prosthetics require a complex structure, adding to overall size, weight, and cost, which can render them impractical for use in daily activities.

In fields unrelated to tremor management and treatment, the use of active stabilizing handgrips is known for rifles and other devices involving azimuth and elevation control of a person's aim. See, for example, U.S. Patent Application Publication No. 2006/0194173 which discloses various embodiments of a handgrip that uses shape memory alloy (SMA) wires to effect elevation and azimuth stabilization.

SUMMARY OF THE INVENTION

In accordance with one aspect of the invention, there is provided a handheld device for canceling unintentional muscle movement. The device includes a base comprising a handgrip for a user to hold, a gripping element linked to the base for releasably connecting the handheld device to an object, a sensor that detects movement of the base, a controller linked to the sensor, and at least one actuator that operates under control of the controller to cause movement of the gripping element in a direction that at least partially counteracts the detected movement of the base.

In accordance with another aspect of the invention, there is provided a handheld device such as described in the preceding paragraph wherein the actuator utilizes SMA wires selectively heated by a power source under control of the controller to effect the movement of the gripping element.

BRIEF DESCRIPTION OF THE DRAWINGS

One or more preferred exemplary embodiments of the invention will hereinafter be described in conjunction with the appended drawings, wherein like designations denote like elements, and wherein:

FIGS. 5A and 5B show assembled and exploded perspective views, respectively, of a handheld device such as in FIG. 1;

DETAILED DESCRIPTION OF THE PREFERRED EMBODIMENTS

As discussed below in connection with the illustrated embodiment, tremor management can be effectuated through the use of a handheld active cancellation device. This handheld device in general detects unintended movement of the device and utilizes at least one actuator operated by a controller in the device to at least partially cancel the unintended movement of the device. Any suitable actuator(s) can be used, including electromagnetic (motor, voice coils, solenoids, etc), pneumatic, and hydraulic as well as smart materials actuation like SMA, piezoelectric, magnetostrictive, electrostrictive, dielectric elastomer, and electro-active polymer actuators. In the illustrated embodiment, the handheld device utilizes a shape memory alloy (SMA)-actuated platform acting between the user's hand and an object to be stabilized. Although SMA wires are used in this embodiment, it will be appreciated that other SMA-based embodiments can be implemented using other types of SMA components such as SMA springs, torque tubes, thin films, sheets, or cables, or some combination of these. By sensing the user's tremor, the handheld device can provide force and displacement to the object in at least a two degree-of-freedom (DOF) plane counteracting any unintended motions while allowing the user's hand to move freely. This approach can heighten user comfort and aids intuitive operation as intended motions can be distinguished from unintended tremor in the handheld device. Tremor cancellation requires less force than tremor suppression because it does not fight the user's muscle action.

Figure 1:
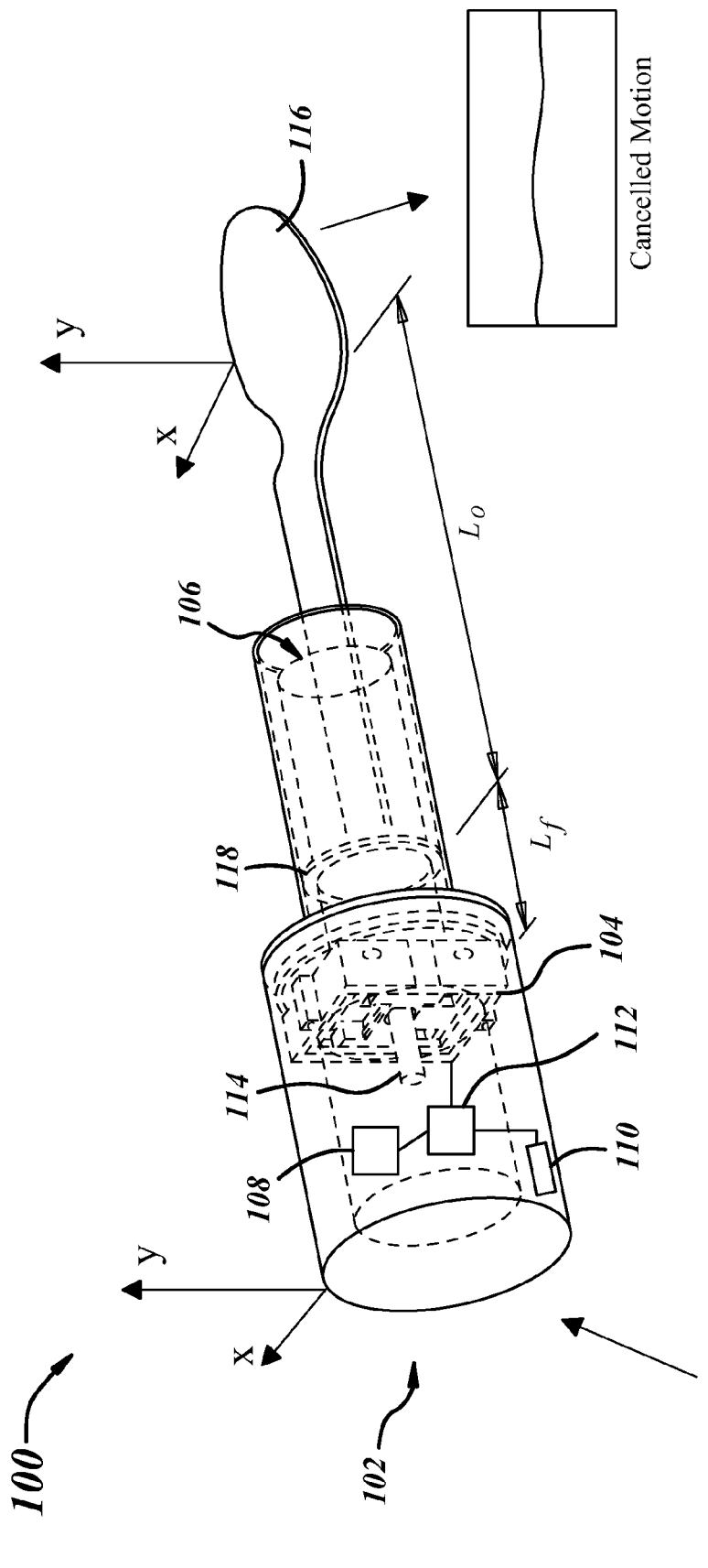
FIG. 1 is an embodiment of a handheld device for canceling unintentional muscle movement constructed in accordance with the invention.

Tremor can be rhythmic and oscillatory in nature. An active cancellation system based on a handheld SMA-actuated stabilization platform can compensate for the tremor. The handheld device can be designed to hold and stabilize various objects (e.g. eating utensils, tools, pointing implements, etc.) by sensing the user's tremor and moving the object or base in an opposite direction using a stabilizing assembly directed by a controller. Referring now to the drawings, FIG. 1 depicts an embodiment of a handheld device for canceling unintentional muscle movement. The device 100 includes a base 102 comprising a handgrip for a user to hold, a stabilizing assembly 104 that can compensate for a user's tremors, and a gripping element 106 linked to the stabilizing assembly 104 for releasably connecting the handheld device 100 to an object 116 such as a spoon that extends into the gripping element 106 along an axis. The gripping element 106 can include an opening in its free end and be designed to accept any of numerous standard implements and objects (e.g., silverware, pens, pencils, etc.) such that the handheld device can be used without requiring specialized implements or other attachments. The stabilizing assembly 104 acts as an actuator that controls movement of the gripping element 106 in a plane normal to this axis, and these two components can be interconnected via a shaft 114 that extends from the actuator 104 to the gripping element 106. As shown in FIG. 1, the gripping element 106 can be an inner cylindrical housing that is supported in an outer cylindrical housing via an elastomeric O-ring 118 that acts as a fulcrum to transfer x-y motion of the shaft 114 at the actuator into x-y motion of the inner cylindrical housing. The base 102 includes a power source 108 for providing current and a sensor 110 used to detect movement of the base 102.

The sensor 110 can be one that measures one or more of the following: inertial position, velocity, acceleration and angular position, velocity, or acceleration in the x, y, and z axes. The power source 108 and sensor 110 are connected to a controller 112 that operates the stabilizing assembly 104 to control movement of the gripping element 106. A cooling system, including a coolant (not shown in FIG. 1), can also be provided for cooling the stabilizing assembly 104. These elements will be shown and discussed in greater detail below.

Figure 2A:
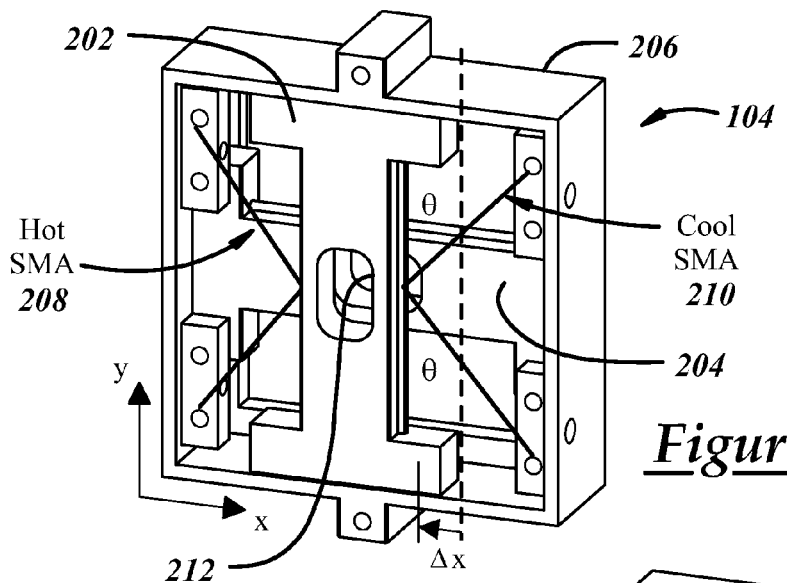
FIGS. 2A-2C show an embodiment of a stabilizing assembly that can be used in the device of FIG. 1, with the assembly shown in three different positions that provide x-axis adjustment of an object controlled by the handheld device.
Figure 2B:
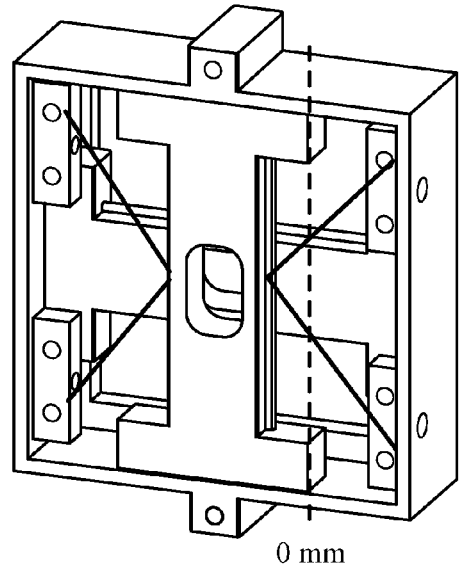
Figure 2C:
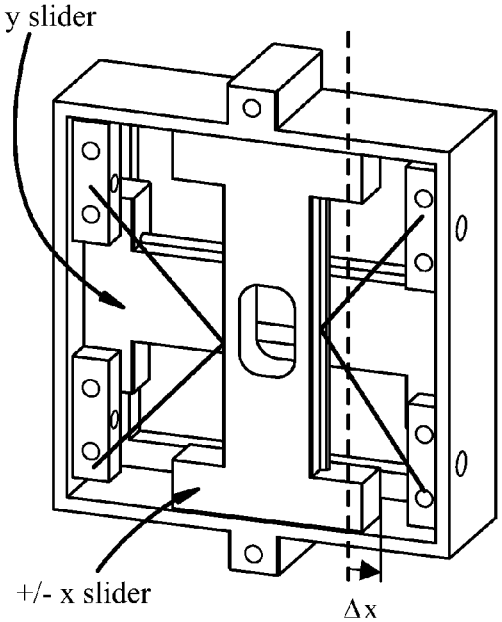

Turning to FIGS. 2A-2C, an embodiment of the stabilizing assembly 104 is shown. The stabilizing assembly 104 can include a first slide 202 and a second slide 204, each supported by a housing 206. The first slide 202 and the second slide 204 can be moved along an x-axis and a y-axis, respectively, using shape memory alloy (SMA) wires. In one embodiment, the first slide 202 can be pulled in one direction along the x-axis using a first SMA wire 208 attached to the left side of the housing 206 at two points and attached to the first slide 202 at a single point. The single point attachment at the first slide 202 can be fixed or alternatively can include a pulley through which the first SMA wire 208 passes. Similarly, the first slide 202 can be pulled in a second, opposite direction along the x-axis using a second SMA wire 210 linked to the right side of the housing 206 at two points and the first slide 202 at one point like the first SMA wire 208. The first slide 202 and second slide 204 can each also include an opening 212, such as a slot, for receiving an output shaft 114 capable of transmitting the movement of the first slide 202 and/or the second slide 204 into movement of the gripping element 106 and ultimately the object shown in FIG. 1.

In this implementation, the configuration of the first SMA wire 208 and the second SMA wire 210 create an antagonistic force between the wires 208, 210. Or in other words, the first SMA wire 208 is generating force in an opposite direction from the second SMA wire 210 and vice-versa. The first SMA wire 208 and the second SMA wire 210 can be electrically connected to the power source 108 that is housed by the base 102 shown in FIG. 1. The controller 112 operates to selectively apply current to the first SMA wire 208 and/or the second SMA wire to generate movement in a desired direction. The first SMA wire 208 and/or the second SMA wire 210 can be electro-resistively heated with the applied current thereby creating a thermo-mechanical transformation in the microstructure of the alloy. This transformation can change the microstructure of the SMA wire 208, 210 from Martensite (low order; stable at high temperature) to Austenite (highly ordered; stable at high temperature). In one example, this transformation can cause the first SMA wire 208 to recover its initial austenitic shape and contract. When the first SMA wire 208 contracts, it simultaneously deforms the second SMA wire 210 that exists in a cool martensitic state and moves the first slide 202 toward the side of the housing 206 where the first SMA wire 208 is attached. Conversely, the first SMA wire 208 can exist in the cool martensitic state while a current is applied to the second SMA wire 210. In this case, the second SMA wire 210 contracts while the first SMA wire 208 is deformed and the first slide 202 moves toward the side of the housing 206 on which the second SMA wire 208 is attached. Further details concerning SMA operation and use as a stabilizing actuator, as well as other actuating technologies, are disclosed in U.S. Patent Application Publication No. 2006/0194173 to Lavigna et al., the complete contents of which are hereby incorporated by reference.

As can be appreciated from FIGS. 2A-2C, the movement of the first slide 202 and the second slide 204 has the effect of shifting the opening 212 around in a plane. The opening 212, when linked to the output shaft of the gripping element 106 shown in FIG. 1 translates the movement along the x-axis into movement of the gripping element 106 and ultimately movement of the object 116. Using this arrangement, the controller can selectively direct current supplied from the power source to the first SMA wire 208 and/or the second SMA wire 210 and move the first slide 202 along the x-axis—as shown in FIGS. 2A and 2C, left and right, respectively, depending on the current supplied. FIGS. 2A-2C also depict the second slide 204 that moves along the y-axis and is controlled by a third SMA wire and a fourth SMA wire. While the third SMA wire and the fourth SMA wire are not shown, in this embodiment the wires attach to the housing much like the first SMA wire 208 and the second SMA wire 210. The third SMA wire and fourth SMA wire can receive selectively directed current from the power source 108 via controller 112 and move the second slide 204 along the y-axis—up and down—depending on the current supplied.

It is anticipated that the first slide 202, the second slide 204, and the housing 206 can be constructed from a variety of materials. For instance, in one embodiment the first and second slide 202, 204, and even the housing 206 can be fashioned from Delrin™ and benefit from its low-friction properties. However, other materials can be used.

The stabilizing assembly 104 can also be adapted in a variety of ways. For instance, it is possible to realize movement of the gripping element 106 in a third dimension, such as along the z-axis. In one example, the entire stabilizing assembly can be moved along the z-axis using SMA wire actuated by electrical current provided by the power source, with this z-axis movement being applied to the shaft 114. In another example, a third slide can be incorporated into the housing 206 using SMA wire arrangements described above. In yet another embodiment, a separate actuator mechanism can be used to apply z-axis movement directly to the shaft 114.

Additionally, the stabilizing assembly shown in FIGS. 1 and 2 can be used with a cooling system. The cooling system can employ a cooling medium—such as a coolant—that speeds the cooling of the SMA wires when current is no longer applied. For instance, in one implementation the stabilizing assembly 104 can be immersed in a cooling chamber located in the base. The cooling chamber can be filled with a suitable cooling medium (coolant). Where a liquid coolant that flows is used, such as distilled water, suitable seals can be used about the shaft 114 and incoming leads that connect to the SMA wires. Or, the O-ring shown in FIG. 1 to support the gripping element 106 can be used to provide a suitable seal against coolant leakage. For a coolant that is more in the form of a paste, such as thermal grease, no seals may be needed. Other suitable coolants will be known to those in the art.

Figure 3:
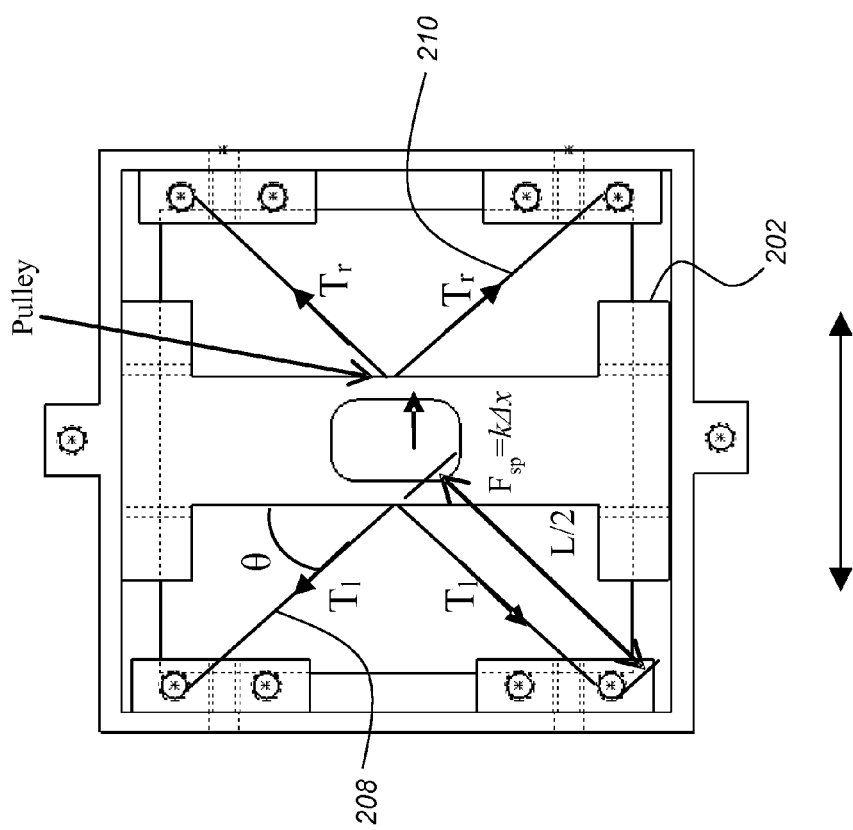
FIG. 3 is a diagram showing further details of operation of the x-axis slider used in the stabilizing assembly of FIGS. 2A-2C.

A more detailed depiction of the first slide described above is shown in FIG. 3. The angled packaging architecture of the SMA wires relates the stress and strain of the SMA wires (e.g. the first through fourth SMA wires) to the output force and displacement of the motion-generating mechanism. As shown in FIG. 3, a continuous segment of SMA wire, such as the first SMA wire 208 or the second SMA wire 210, can be used for movement along the x-axis, where the wire is passed through a pulley that is attached to the first slide 202. While the following will be described in relation to the first slide 202 and the first and second SMA wires 208, 210, it is equally applicable to the second slide 204 and the third and fourth wires (i.e. movement along the y-axis).

In this configuration the each SMA wire can substantially form a V-shape, with an angle θ from horizontal. In some implementations, a spring having a compliance of k can move the first slide 202 to its neutral position under zero power/current and can provide a force ($F_{sp}$) proportional to the output displacement. A relationship between wire tensions can be expressed as, $$2T_r \sin\theta + F_{sp} = 2T_l \sin\theta, \quad (1)$$

where $T_l$ and $T_r$ are representative of tensions in the first SMA wire 208 and the second SMA wire 210, respectively. This relationship can be related to SMA wire strain through an energy balance as, $$T_l L \Delta\epsilon = 2T_l \sin\theta \Delta x. \quad (2)$$

where $\Delta x$ can denote the displacement of the first slide 202. Rearranging the energy balance shown above in equation (2) yields a relationship between the change in strain of the first and second SMA wires 208, 210 ($\Delta\epsilon$) and the output displacement of the first slide 202 ($\Delta x$), $$\Delta x = \frac{L\Delta\varepsilon}{2\sin\theta}, \quad (3)$$

which is related to the motion of the object $\Delta x_0$ being stabilized through a simple leverage, $$\Delta x_o = \frac{L_o}{L_f} \Delta x. \quad (4)$$

Knowing that the spring force, $F_{sp}$, in the force balance equation (1) is equal to an external spring stiffness constant k multiplied by $\Delta x$, the displacement equation (3) can be substituted into the force balance equation (1) producing, $$T_r + \frac{kL\Delta\varepsilon}{4\sin^2\theta} = T_l. \quad (5)$$

Dividing both sides of the modified force balance equation (5) by the cross-sectional area, A, of an SMA wire produces an expression relating the stress in the first SMA wire 208 and the second SMA wire 210

$$\sigma_r + \tilde{k}_{eq} L(\epsilon_r - \epsilon_N) = \sigma_l, \quad (6)$$

where $\Delta\epsilon$ can be defined as the difference of the strain in the right wire $\epsilon_r$ from the neutral strain $\epsilon_N$, and the equivalent spring stiffness can be represented as $$\tilde{k}_{eq} = \left(\frac{k}{4A\sin^2\theta}\right). \quad (7)$$

Since the kinematic equations (4) and (6) can relate the stress and strain of the first SMA wire 208 and the second SMA wire 210 to the output motion of the object, it is helpful to know the transient behavior of the first and second SMA wires 208, 210 (subject to an input current, antagonistic configuration, external stress, and convective heat transfer) in order to predict performance. In an effort to understand the transient behavior, a mathematical model for an stabilizing assembly can consist of three components: a set of differential equations describing the thermo-mechanical phase transformation behavior of the SMA wires, a set of compatibility equations specific to the antagonistic configuration of SMA wires relating stresses and strains in the two wires to each other, and a set of heat transfer equations involving the thermal properties of both the environment and the wire material.

Thermomechanical models for each wire can be derived from a simplified Helmholtz free energy function of the SMA wire, $$\phi(\varepsilon, \xi, T) = \frac{E}{2\rho}[\varepsilon - (\xi_1 - \xi_2)\beta]^2 - \qquad(8)$$
$$(T - T_R)(\xi_1 - \xi_2)\Delta S + (c_o - s_o)(T - T_R) - c_o T \ln\left(\frac{T}{T_R}\right)$$

Simplifications can be made from the assumptions that there is no significant change in Young's modulus between Austenite and Martensite, no free energy of mixing, and no gradients (in any direction) in temperature, strain, or phase fraction eliminating the need for a partial differential equation (PDE). In the free energy function of equation (8), $\varepsilon$ is the strain the wire, T is the temperature, $\beta$ is the maximum recoverable strain under zero stress, E is the Young's modulus, $T_R$ is the reference temperature for phase transformation, $\Delta S$ is the change in entropy due to transformation, $\xi_1$ is the tensile Martensite phase fraction, $\xi_2$ is the compressive phase fraction, and $c_0$ and $s_0$ are material constants relating to the phase-independent specific heat and entropy. The Austenite phase fraction $\xi_3$, is implicit in this system since the Martensite and Austenite phase fractions sum to one. The stress in each wire is defined as the partial derivative of the Helmholtz free energy with respect to strain (holding the other states constant). For each wire (with subscript x replaced with l or r for the first SMA wire 208 or the second SMA wire 210, respectively), $$\sigma_x = \rho \frac{\partial \phi_x}{\partial \varepsilon_x} = E[\varepsilon_x - (\xi_{1,x} - \xi_{2,x})\beta], \qquad(9)$$

where, for example, $\varepsilon_l$ is the strain in the left wire. The partial derivative of the Helmholtz free energy with respect to tensile or compressive Martensite phase fraction relates to a thermodynamic driving force vector $\mu$ for the production of each phase of Martensite lying in the space defined by martensitic phase fractions $\xi_1$ and $\xi_2$. For each wire this can be represented by $$\mu_x = \begin{bmatrix} \mu_{1,x} \\ \mu_{2,x} \end{bmatrix} \qquad(10)$$
$$= \begin{bmatrix} \frac{\beta E}{\rho}[\varepsilon_x - (\xi_{1,x} - \xi_{2,x})\beta] + (T_x - T_R)\Delta s \\ -\frac{\beta E}{\rho}[\varepsilon_x - (\xi_{1,x} - \xi_{2,x})\beta] + (T_x - T_R)\Delta s \end{bmatrix}.$$

To account for hysteresis, phase evolution can occur if the thermodynamic driving force is greater than a critical value, $\mu_c$ by the relation given in, $$\dot{\xi}_x = \begin{bmatrix} 0 & : \text{if } \mu_x \cdot m_x < \mu_c \\ v_o(\mu_x \cdot m_x - \mu_c)m_x & : \text{if } \mu_x \cdot m_x > \mu_c \end{bmatrix}. \qquad(11)$$

Figure 4:
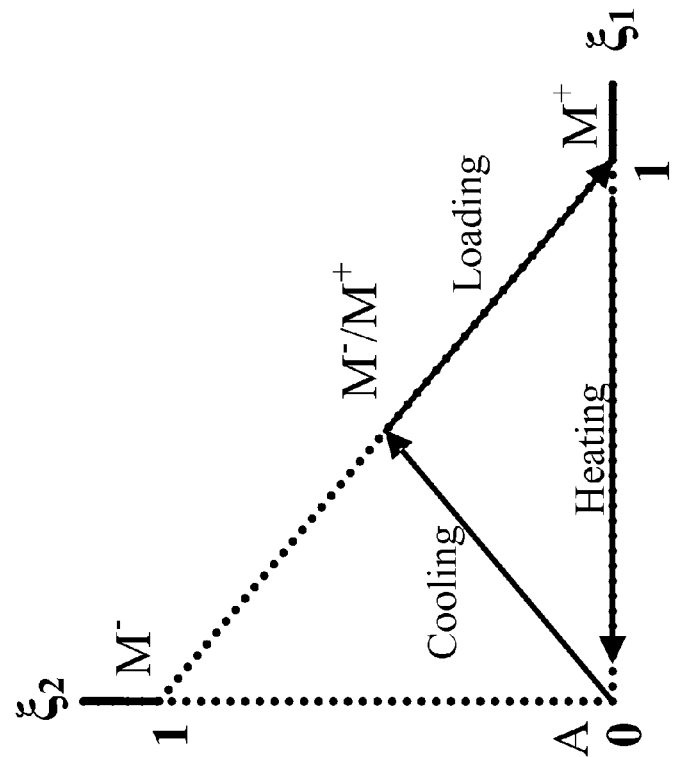
FIG. 4 is a plot of the admissible space for phase fractions of SMA wires used in the stabilizing assembly of the handheld device of FIG. 1.

Since the phase fractions must be non-negative and sum to one, an "admissible space" is represented as the arrowed triangle shown in FIG. 4. The phase transformation equation (11) can employ a unit vector m that depends on the state of the material. This unit vector can be defined as the unit vector of $\mu$ if the phase fractions are either within the interior of the admissible space and not on any boundaries, or if the phase fractions lie on any of the edges, and $\mu$ is pointing inwards. Otherwise, if $\mu$ points outwards, m can be the unit vector of its projection along the boundary. If the phase fractions reside on one of the corners, m can be zero if $\mu$ points directly outward.

The stabilizing assembly shown in FIGS. 2 and 3 uses an antagonistic configuration of the first SMA wire 208 and the second SMA wire 210, whereby each wire can be at least partially described using stress and strain variables. Because many devices are designed to strain the opposing wire to some fraction of the maximum strain $\beta$ (conservatively this can be half) to ensure operation over many cycles, an amount of pre-strain ($P_s$) is incorporated in the strain compatibility equation, $$\varepsilon_r - \varepsilon_l = (\beta - P_s). \qquad(12)$$

The stress induced from one SMA wire to another can be derived in the stress balance equation (6). Depending on the speed of the first slide 202 and second slide 204 relative to its cooling environment, such as provided by the cooling system discussed above, it is possible that one of the SMA wires can become slack near the end of the actuation stroke. This may occur when the power to the heated SMA wire is cut off before the opposing antagonistic SMA wire is heated, which may occur when driving the system at low duty cycles. In such cases, the heated actuating SMA wire is allowed to cool, relaxing under the system spring load and loosening the opposing SMA wire.

When a pair of SMA wires, such as the first SMA wire 208 and the second SMA wire, are taut, then the stress in both wires is positive (tensile). Combining the compatibility equations (6) and (12) with the equation (9) for stress in each wire, an expression for strain in the first SMA wire 208 is found to be $$\varepsilon_l = -\frac{1}{2E + \tilde{k}_{eq}l}\left[E\beta[(\xi_{1,r} - \xi_{2,r}) - (\xi_{1,l} - \xi_{2,l})] + \left(E + \frac{\tilde{k}_{eq}l}{2}\right)(P_s - \beta)\right] \qquad(13)$$

Strain in the second SMA wire 210 can be found by applying the strain compatibility equation (12), $$\varepsilon_r = \beta + \qquad(14)$$
$$\frac{1}{2E + \tilde{k}_{eq}l}\left[E\beta[(\xi_{1,r} - \xi_{2,r}) - (\xi_{1,l} - \xi_{2,l})] + \left(E + \frac{\tilde{k}_{eq}l}{2}\right)(P_s - \beta)\right] - P_s$$

Using the strain equations (13) and (14), the output motion can be calculated using the kinematic displacement equation (4) knowing that the difference of the strain $\Delta \varepsilon$ is the difference between the strain in the right wire $\varepsilon_r$ from the neutral strain $\varepsilon_N$.

If stress in an antagonistic SMA wire goes below zero, the expressions for strain can be adjusted. For instance, if the first SMA wire 202 goes into compression, its stress can be set to zero, $$\sigma_l = 0, \qquad(15)$$

and from the kinematic stress balance, equation (6), $$\sigma_r = \langle \tilde{k}_{eq} l [(\frac{\beta - P_s}{2}) - \varepsilon_r] \rangle. \quad (16)$$

Following the same substitution process used to derive strains in the first SMA wire 208 and the second SMA wire 210 for taut conditions (Equations 13 and 14), formulas for strain in the first and second SMA wires 208, 210 (for the wire slack in the first SMA wire 208) are derived as $$\varepsilon_l = (\xi_{1,l} - \xi_{2,l}) \beta \quad (17)$$

and $$\varepsilon_r = \frac{1}{1 + \frac{\tilde{k}_{eq} l}{E}} \left[ (\xi_{1,r} - \xi_{2,r}) B + \frac{\tilde{k}_{eq} l}{E} (\frac{\beta - P_s}{2}) \right], \quad (18)$$

that can be substituted into the output displacement equation (4). Analogous stress and strain equations for system can be used should the second SMA wire 210 go into compression.

The evolution of temperature over time can be described by a traditional lumped heat equation with an additional latent heat term, derived from a general form. In the following equations, heat can be generated in the wire through electrical resistive heating (by an applied current I) while heat can be lost via convective cooling to the environment. The energy balance in each wire can be described by $$\rho A l c_o \dot{T}_x = \rho A l \left( \mu_x - \left[ \frac{T \Delta S}{T \Delta S} \right] \right) \cdot \dot{\xi}_x - h \pi d l (T_x - T_{amb}) + I_x^2 R_x l \quad (19)$$

where I is the input current to the first SMA wire or second SMA wire 208, 210, R is the wire resistivity (resistance per unit length), and L is the length of wire, h is the convective heat transfer coefficient, and $T_{amb}$ is the temperature of the surrounding environment. Exemplary values of these are listed in Table 1. To predict the stabilizing assembly motion, the material equations (10) and (11), compatibility equations (13) and (14), and heat transfer equation (19) can be solved simultaneously to describe the displacement of the stabilizing assembly as a function of time. The heat equation can be integrated for the first SMA wire 208 and the second SMA wire 210 through a forward time-step scheme to obtain the temperature of the wires over time. The time derivative of $\xi$ can be obtained by substituting the thermodynamic driving force of equations (10) into the kinetic equation (11) for each wire. Using the kinematic displacement equation (4) the wire strains can be translated to displacement.

In one implementation shown in FIGS. 5A and 5B, a handheld device 500 was designed to cancel human tremor of up to 1 mm peak-peak amplitude at 1-4 Hz, which is within the frequency range of large-amplitude unintentional tremor of the arm. The thermo-mechanical material equations (10) and (11), compatibility equations (13) and (14), and heat transfer equation (19) were numerically solved using the material properties and parameters listed in the following table.

TABLE 1

| Symbol | Name | Value | Units |
|---|---|---|---|
| $P_s$ | Prestrain | 1 | % |
| k | Spring Stiffness | 7E+3 | N/m |
| θ | Wire Angle | 40 | degrees |
| β | Max. SMA Strain | 5 | % |
| ρ | Density | 6.5E6 | g/m³ |
| $\mu_c$ | Critical Driving Force | 1.01 | J/g |
| ΔS | Entropy Change | −6.7E−2 | J/gK |
| $T_R$ | Reference Temperature | 323 | K |
| $T_a$ | Ambient Temperature | 296 | K |
| $v_o$ | Kinetic Stiffness | 50 | g/Js |
| E | Young's Modulus | 70 | GPA |

In an experiment measuring cancellation performance, a simple feedback controller was placed in simulation around the model. The controller implemented a tremor disturbance as a base sinusoidal disturbance at an assumed dominant frequency of 3 Hz with 1 mm amplitude. Power input signals were sent by a simulated proportional controller to the handheld device 500, and an output tracking error was measured. Simulations were conducted while the input voltage of the device was held at 12 Volts and the ambient temperature was constant at 24° C. The electrical resistance of the SMA wires was allowed to vary with wire diameter with a relationship based on curve fits of data obtained by the wire manufacturer.

The handheld device 500 maintained the operating stress of the SMA wires below 270 MPA to prevent performance losses over many cycles. This device in this implementation used 1.5 inches of 8 mil diameter SMA wire for each of the first SMA wire 508, the second SMA wire 510, the third SMA wire (not shown), and the fourth SMA wire (also not shown), running on a proportional feedback gain of 4. A cooling medium of distilled water was chosen as a coolant 506 in the cooling system. Using this implementation 500 of the device, the actuator 512 was calculated to draw 12.1 watts while operating in this medium.

SMA wires (70° C. Flexinol™) were used (available from Dynalloy Inc. of Costa Mesa, Calif.) that were 1.5 inches long and 8 mil in diameter. Distilled water was selected as a coolant 506 and was contained by an acrylic chamber 504 bored from cylindrical stock in a manner that can be appreciated by those in the art. The acrylic chamber 504 is located in the base 502 and was designed to receive the stabilizing assembly 512 within the chamber. The coolant 506 in the acrylic chamber surrounds the SMA wires and provides an increased cooling effect after the SMA wires have been heated. Electrical connections can be made to the SMA wires through a water-sealed rubber grommet. Output from the stabilizing assembly 512 was transmitted through an output shaft in the form of a steel pin 514 to an movable cylinder 516 (the gripping element) that was held in place with a rubber O-ring 518. The rubber O-ring 518 can provide stiffness to help the gripping element 516 return to a neutral position under zero load and seal the coolant inside the base. To control the stabilizing assembly 512, an embedded sensor/controller package (not shown) was included with the base 502. An IDG300 dual axis MEMS gyro sensor was selected to control angular deviations of the base due to tremor, and the signals output from this sensor was read by an ATMEGA16 microcontroller.

During tests of this implementation, the tremor cancellation device balanced on its center of mass and pivoted in the vertical direction. The bottom of the handheld device was attached to a LabWorks™ 139-40 Electrodynamic Shaker System that was controlled by a laptop running Labview™. The shaker system varied sinusoidal disturbances of approximately 1 mm peak-peak at 1, 3, and 5 Hz, and a recorded human tremor signal. In one implementation, a laser displacement sensor fed-back the output position of the base to the controller, which applied the same gain that was calculated during antagonistic model simulation studies. However, in another implementation an embedded sensor/controller solution was also tested, and in these experiments the feed-back signal consisted of the angular rate of the user's tremor, allowing for slow intended tracking motions. In each series of tests, an A/D converter of the controller sampled the feed-back signals at 5 Khz. Depending on whether the input to the microcontroller was above or below a reference signal, the microcontroller output a duty cycle signal of 60 Hz to a MOSFET transistor that was responsible for switching 12 volts to the appropriate SMA wire. The laser displacement sensor recorded the resulting output motion of the stabilized object, and tests were conducted at each of the frequencies of interest along with the human tremor signal.

Figure 6:
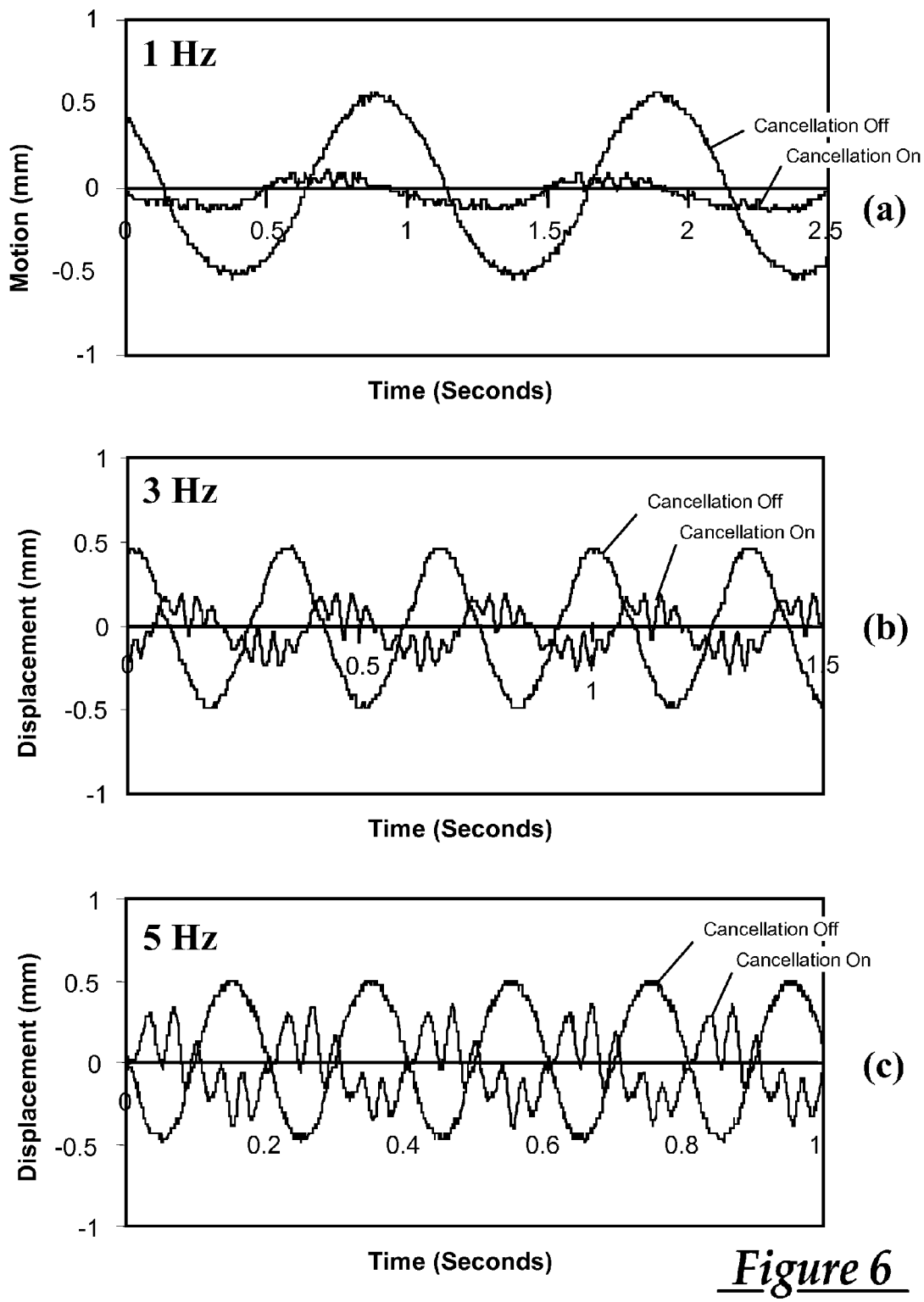
FIG. 6 shows charts showing the effect of cancellation control by a handheld device such as in FIG. 5 using a laser displacement sensor at sinusoidal input disturbances of different frequencies.

Human tremor is often characterized as being sinusoidal in nature with a dominant frequency. As a result, initial cancellation tests focused on demonstrating closed-loop control of single-frequency sinusoidal disturbances. Three different frequency levels were chosen (1, 3, and 5 Hz) to test the handheld device in the design frequency range of 1-4 Hz and also outside at 5 Hz. The charts in FIG. 6(a)-(c) show the cancellation results for position control using the laser displacement sensor.

At 1 Hz, significant motion cancellation was achieved with 82% peak-peak and 80% RMS signal reductions. At 3 Hz, some performance degradation was recorded, which was likely due to the simple proportional control. At this frequency, 61% RMS cancellation was produced with a peak-peak reduction of 72%. Since the proportional gain was set to the same value as the one calculated during simulation, these favorable results demonstrate the value of the model-based design. In the table above, the handheld device is also tested outside its design range at 5 Hz.

Figure 7:
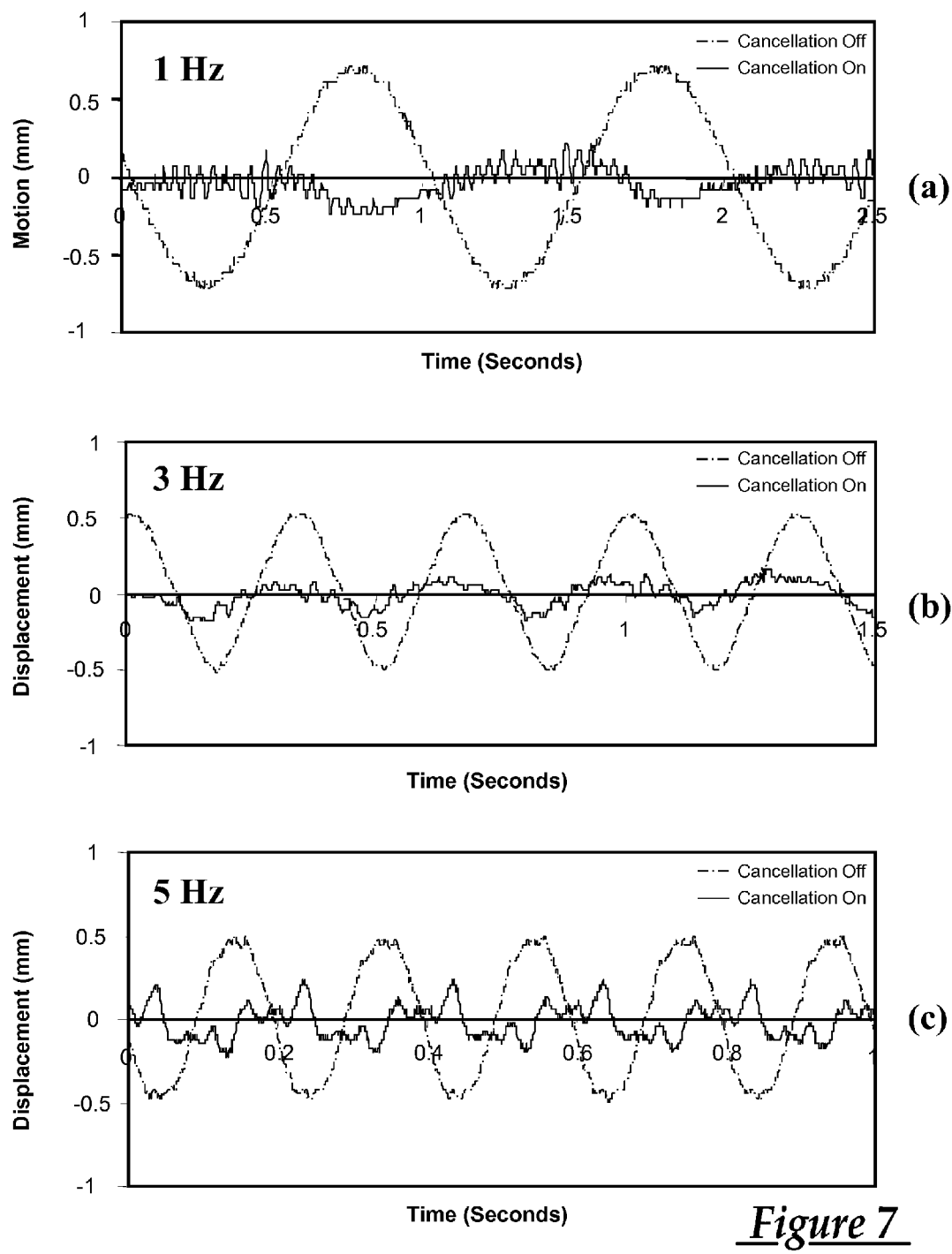
FIG. 7 shows charts showing the effect of cancellation control by a handheld device such as in FIG. 5 using a MEMS gyro rate sensor at sinusoidal input disturbances of different frequencies.

Tests using a MEMS gyro rate sensor were also conducted to demonstrate functionality using a completely embedded solution that stabilizes the rate of disturbance and differentiating between relatively high-frequency tremor and slow intended motions. The charts in FIG. 7(a)-(c) show the cancellation performance under angular rate control at each of the tested frequencies, demonstrating considerable disturbance cancellation.

For example, at 1 Hz a reduction of 67% peak-peak amplitude is achieved along with an RMS cancellation of 78%, which is only slightly lower than results obtained using the laser displacement sensor. At 3 Hz, substantial cancellation was also observed as the peak-peak amplitude was reduced by 70% along with an RMS cancellation of 75%. This performance improves upon the laser displacement sensor tests indicating that the rate control may be suitable for higher frequencies, as the rate feedback amplitude increases with frequency. At the upper frequency bound of 5 Hz, however, difficulties in cancellation begin to arise. The cancelled signal in the table above shows a peak-peak cancellation of 53%, which is 17% less than that observed for 3 Hz. An RMS cancellation of 69% was calculated, which is also 6% lower than the cancellation calculated for 3 Hz. This loss in performance may be due to actuator performance losses. However, since the stabilizing assembly was optimized to cancel base tremors near 3 Hz, this degradation in performance at the upper frequency bound of 5 Hz can be expected. In all of the cancelled signals a small amplitude high-frequency (25-30 Hz) component can be present due to the excitation of a natural frequency in the system due to un-modeled inertia.

Both of the single-frequency tests represented in the above tables can demonstrate significant cancellation for the 1-4 Hz frequency range. Because the identified tremor resides in this same frequency range, considerable stabilization of a human tremor signal should be expected. For handheld devices canceling tremors at higher frequencies, performance can be improved through a model-based redesign using a higher frequency specification.

In yet another experiment, tremor cancellation performance was measured while inputting a tremor signal to the device whereby the device received the signal from a healthy volunteer who was instructed to hold the handheld device steady while in its off state. During this time, the tip displacement of the device was recorded with the laser displacement sensor and its output was displayed on an oscilloscope to give the volunteer visual feedback. The recorded motion exhibits a peak-peak amplitude of approximately 1.5 mm. The frequency content indicated that the dominant frequencies in the recorded tremor signal (for the healthy individual) are mainly below 3 Hz. This result is consistent with the design of the cancellation device, which was shown to perform with no degradation in cancellation performance up to 3 Hz. The amplitude of the frequency components above 3 Hz are very small, indicating that the performance degradation demonstrated by the single-frequency tests at 5 Hz is not a significant issue for this case.

Figure 8:
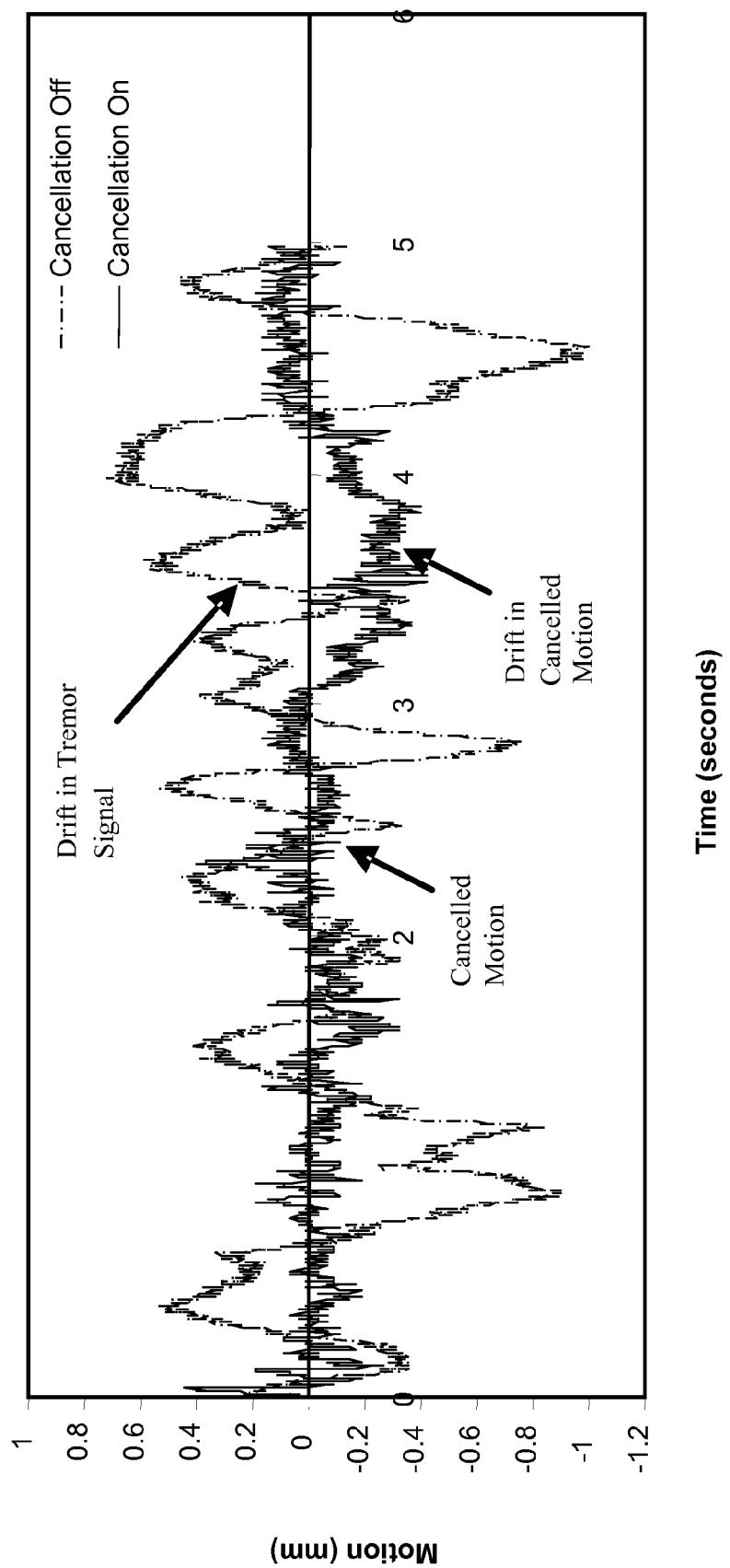
FIG. 8 shows a chart depicting the result of tremor cancellation using a handheld device such as in FIG. 5 to cancel a recorded input tremor used for physical disturbances of the device via shaker test device.

Tests on the tremor cancellation device were conducted outputting a recorded tremor signal from the laptop running LabView™. This signal was fed into a shaker amplifier, causing the shaker to replicate the five seconds of recorded tremor repeating in a loop. In the plot of FIG. 8, the resulting tip displacement is plotted with the tremor cancellation device on (using the MEMS gyro for motion sensing) and off. The resultant plot with the tremor cancellation device activated shows that most of the sharp peaks are cancelled, and the output motion remains near the zero position, proving the active tremor cancellation concept. After the 3-second mark in the FIG. 8 plot, the cancelled motion does begin to drift from this zero position, though this is due to the fact that the tremor disturbance signal drifts in its neutral position as well. Neglecting this drift, the overall cancellation is 71% RMS, which is only 7% lower than the cancellation produced during the 1 Hz single-frequency disturbance test. The FFT of the cancelled signal also reflects the significant reduction, where only low-frequencies that are in the same range as tracking motions are preserved.

Overall, the cancellation results demonstrate the success of the model-based design of the SMA actuator. Because proper specifications were identified for the human tremor, the actuator was simulated numerically using various design variables. Through simulation, a design was identified that was capable of producing cancellation at the upper frequency bound of 3 Hz (and below), and this design was experimentally tested to perform as designed using a simple controller.

In addition to cancellation performance, power consumption was also studied in simulation. Tests compared the actual power consumption to that predicted by the thermo-mechanical SMA model. During the experiments, the input power was monitored at 3 Hz, and the average consumption was calculated to be 11.20 Watts, which is only 7% lower than the power draw of 12.07 Watts that was predicted during simulation. The small deviation from the experimental to simulated power draw again demonstrates the significant utility of the design model since this result proves that it was successful in calculating a design with minimal energy consumption. Assuming a NiMH battery is used to power the cancellation device in two degrees of freedom (thus twice the measured power consumption), and that an approximate energy density for NiMH is 70 Wh/Kg, approximately 160 grams battery weight could be used for 30 minutes of operation. If weight were a significant issue, more expensive lithium ion batteries could be employed that weigh only 70 grams for the same 30 minutes of operation, assuming energy densities of 160 Wh/Kg.

It is to be understood that the foregoing is a description of one or more preferred exemplary embodiments of the invention. The invention is not limited to the particular embodiment(s) disclosed herein, but rather is defined solely by the claims below. Furthermore, the statements contained in the foregoing description relate to particular embodiments and are not to be construed as limitations on the scope of the invention or on the definition of terms used in the claims, except where a term or phrase is expressly defined above. Various other embodiments and various changes and modifications to the disclosed embodiment(s) will become apparent to those skilled in the art. For example, actuators other than SMA materials could be used to provide the desired stabilization. Also, while the disclosed embodiments involved pivoting of the gripping element about its O-ring mounting position rather than a pure translational movement, any suitable type of x-y movement can be used to cancel tremor. Furthermore, as noted above, an axially-directed (z-axis) adjustment can be used to provide three dimensional tremor cancellation. All such other embodiments, changes, and modifications are intended to come within the scope of the appended claims.

As used in this specification and claims, the terms "for example," "for instance," "such as," and "like," and the verbs "comprising," "having," "including," and their other verb forms, when used in conjunction with a listing of one or more components or other items, are each to be construed as open-ended, meaning that the listing is not to be considered as excluding other, additional components or items. Other terms are to be construed using their broadest reasonable meaning unless they are used in a context that requires a different interpretation.

The invention claimed is:

1. A handheld device for canceling unintentional muscle movement, comprising:
    a base comprising a handgrip for a user to hold;
    a gripping element linked to the base for releasably connecting the handheld device to an object;
    a sensor configured to detect movement of the base;
    a controller linked to the sensor; and
    at least one actuator configured to operate under control of the controller and configured to cause movement of the gripping element in a direction that is at least partially counteractive to the detected movement of the base, wherein the actuator(s) comprises at least one shape memory alloy (SMA) component configured to control movement of the gripping element along a first axis and at least one other SMA component configured to control movement of the gripping element along a second axis that is orthogonal to the first axis.

2. The handheld device of claim 1, wherein the object connects to the gripping element along a third axis and wherein the actuator(s) are configured to cause the movement of the gripping element within a plane that is normal to the third axis.

3. The handheld device of claim 2, wherein the actuator(s) are configured to also cause movement of the gripping element along the third axis.

4. The handheld device of claim 1, wherein the object is received within the gripping element along a third axis that is orthogonal to the first and second axes.

5. The handheld device of claim 1, further comprising coolant in contact with the SMA components.

6. The handheld device of claim 1, further comprising a power source configured to be used by the controller to selectively heat the SMA components.

7. The handheld device of claim 1, wherein the SMA components each comprise at least one SMA wire, spring, torque tube, thin film, sheet, or cable.

8. The handheld device of claim 1, further comprising an outer cylindrical housing connected to the base, and wherein the gripping element comprises an inner cylindrical housing mounted within the outer cylindrical housing and being pivotable relative to the outer cylindrical housing.

9. The handheld device of claim 8, further comprising a shaft interconnecting the actuator(s) with the gripping element, the actuator(s) configured to pivot the gripping element within the outer cylindrical housing by being configured to cause movement of the shaft in a plane normal to an axis of the outer housing.

10. A handheld device for canceling unintentional muscle movement, comprising:
    a base comprising a handgrip for a user to hold;
    a gripping element linked to the base for releasably connecting the handheld device to an object that extends away from the base at least generally along an axis;
    a first shape memory alloy (SMA) wire configured to actuate the gripping element in a first direction along an x-axis;
    a second SMA wire configured to actuate the gripping element in a second direction along the x-axis;
    a third SMA wire configured to actuate the gripping element in a first direction along a y-axis;
    a fourth SMA wire configured to actuate the gripping element in a second direction along the y-axis, wherein the gripping element moves in at least two dimensions within a plane defined by the x-axis and y-axis and substantially normal to the axis of the object;
    a power source electrically connected to the SMA wires for selectively providing current to the SMA wires;
    a sensor configured to detect movement of the base;
    a controller linked to the power source and the sensor, wherein the controller is configured to operate in response to the sensor and is configured to selectively control the flow of current from the power source to the SMA wires; and
    a cooling system having coolant that cools at least some of the SMA wires.

11. The handheld device of claim 10, wherein the gripping element further comprises a first element providing x-axis movement, wherein the first element is configured to be acted on by the first SMA wire and the second SMA wire.

12. The handheld device of claim 11, wherein the first SMA wire and the second SMA wire are in an antagonistic configuration.

13. The handheld device of claim 11, wherein the gripping element further comprises a second element configured to provide y-axis movement, wherein the second element is configured to be acted on by the third SMA wire and the fourth SMA wire.

14. The handheld device of claim 13, wherein the third SMA wire and the fourth SMA wire are in an antagonistic configuration.

15. The handheld device of claim 13, wherein the first element and the second element are oriented substantially parallel to each other.

16. A handheld device for canceling unintentional muscle movement, comprising:
 a base comprising a handgrip for a user to hold;
 a gripping element linked to the base for releasably connecting the handheld device to an object that extends away from the base at least generally along an axis;
 a stabilizing assembly between the base and the gripping element, comprising:
 a first slide linked to the gripping element for adjusting the gripping element in two directions along an x-axis;
 a second slide linked to the gripping element for adjusting the gripping element in two directions along a y-axis;
 a housing assembly supporting the first slide and the second slide for permitting the first slide and second slide to travel a predetermined distance along their respective axes, wherein the adjustment of the first slide and the adjustment of the second slide is substantially parallel to each other;
 a first shape memory alloy (SMA) wire configured to actuate the first slide of the stabilizing assembly in a first direction along an x-axis;
 a second SMA wire configured to actuate the first slide of the stabilizing assembly in a second direction along the x-axis;
 a third SMA wire configured to actuate the second slide of the stabilizing assembly in a first direction along a y-axis;
 a fourth SMA wire configured to actuate the second slide of the stabilizing assembly in a second direction along the y-axis, wherein the object gripped by the gripping element is positioned in a direction substantially normal to a plane defined by the x-axis and the y-axis;
 a power source electrically connected to the SMA wires for selectively providing current to the SMA wires;
 a sensor configured to detect movement of the base; and
 a controller linked to the power source and the sensor, wherein the controller is configured to operate in response to the sensor and is configured to selectively control the flow of current from the power source to the SMA wires.

17. The handheld device of claim 16, wherein the first SMA wire and the second SMA wire are in an antagonistic configuration.

18. The handheld device of claim 17, wherein the third SMA wire and the fourth SMA wire are in an antagonistic configuration.

19. The handheld device of claim 16, further comprising a cooling system for providing coolant to cool the SMA wires.

20. A handheld device for canceling unintentional muscle movement, comprising:
 a base comprising a handgrip for a user to hold;
 a gripping element linked to the base for releasably connecting the handheld device to an object;
 a sensor configured to detect movement of the base;
 a controller linked to the sensor; and
 at least one actuator configured to operate under control of the controller and configured to cause movement of the gripping element in a direction that is at least partially counteractive to the detected movement of the base, wherein the actuator(s) comprises at least one smart material actuation component configured to control movement of the gripping element along a first axis and at least one other smart material actuation component configured to control movement of the gripping element along a second axis that is orthogonal to the first axis.

21. The handheld device of claim 20, wherein the actuator(s) comprises at least one shape memory alloy, piezoelectric, magnetostrictive, electrostrictive, dielectric elastomer, or electro-active polymer actuator.

* * * * *